United States Patent
Berke et al.

(10) Patent No.: US 6,647,992 B2
(45) Date of Patent: *Nov. 18, 2003

(54) AEROSOL APPARATUS FOR HEALTH, HYGIENIC AND GROOMING NEEDS

(75) Inventors: Joseph J. Berke, 3248 Interlaken, West Bloomfield, MI (US) 48323; Charles T. Michael, Troy, MI (US)

(73) Assignee: Joseph J. Berke, West Bloomfield, MI (US)

( * ) Notice: Subject to any disclaimer, the term of this patent is extended or adjusted under 35 U.S.C. 154(b) by 103 days.

This patent is subject to a terminal disclaimer.

(21) Appl. No.: 09/921,772

(22) Filed: Aug. 3, 2001

(65) Prior Publication Data

US 2001/0047807 A1 Dec. 6, 2001

Related U.S. Application Data

(62) Division of application No. 09/458,732, filed on Dec. 13, 1999, now Pat. No. 6,269,821.

(51) Int. Cl.[7] .............................................. A45D 40/24
(52) U.S. Cl. ...................................................... 132/317
(58) Field of Search ................................. 132/112, 317, 132/320; 401/190, 187; 222/402.1, 402.11, 402.013, 402.015, 527, 529; 239/396, 569

(56) References Cited

U.S. PATENT DOCUMENTS

| | | | | | |
|---|---|---|---|---|---|
| 3,637,141 | A | * | 1/1972 | Gores | 239/326 |
| 3,784,063 | A | * | 1/1974 | Otis et al. | 222/394 |
| 3,964,501 | A | * | 6/1976 | Matchett | 132/112 |
| 3,973,853 | A | * | 8/1976 | Myers | 401/190 |
| 4,717,278 | A | * | 1/1988 | Kemeny | 401/286 |
| 5,098,291 | A | * | 3/1992 | Curtis et al. | 433/89 |
| 6,000,405 | A | * | 12/1999 | De Laforcade | 132/116 |

* cited by examiner

*Primary Examiner*—Eduardo C. Robert
(74) *Attorney, Agent, or Firm*—Alex Rhodes

(57) ABSTRACT

An aerosol apparatus for applying health or beauty products to selected portions of a person's body. The apparatus is suitable for general use but provides major benefits to physically disadvantaged persons, such as elderly, arthritic, amputee, paralytic and bedridden persons who are unable to care for their hygienic, health and grooming needs. The apparatus is suitable for use in residences, hospitals, nursing homes, at the beach and while traveling. The apparatus is comprised of a replaceable aerosol cartridge, a slender elongated tubular member having an inlet portion operatively connected to the cartridge, and an applicator attached to an outlet portion of the tubular member. The applicator can be rotatable about three mutually perpendicular axes for applying health and beauty products to difficult to reach body areas. The elongated tube may be extensible to provide further utility.

16 Claims, 6 Drawing Sheets

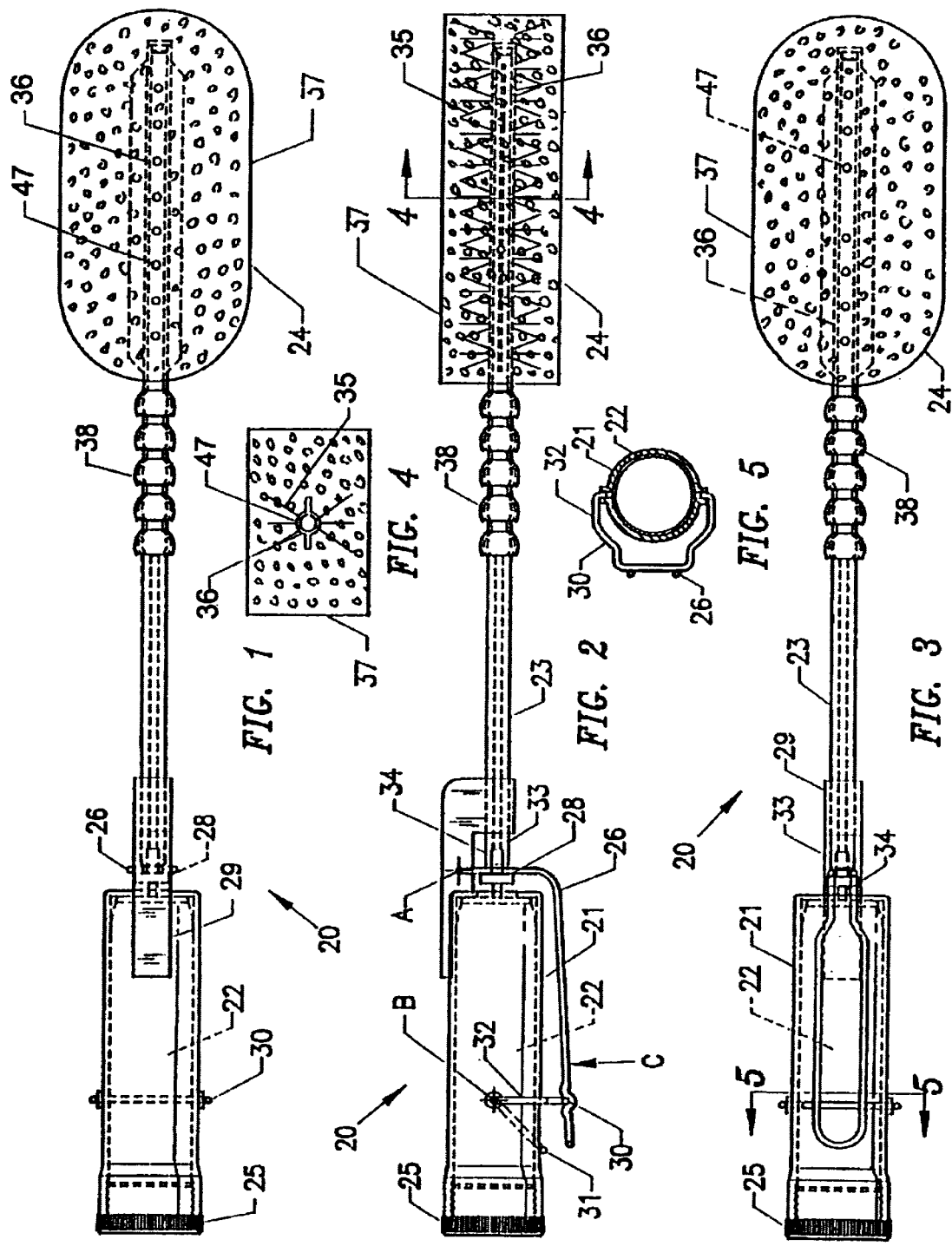

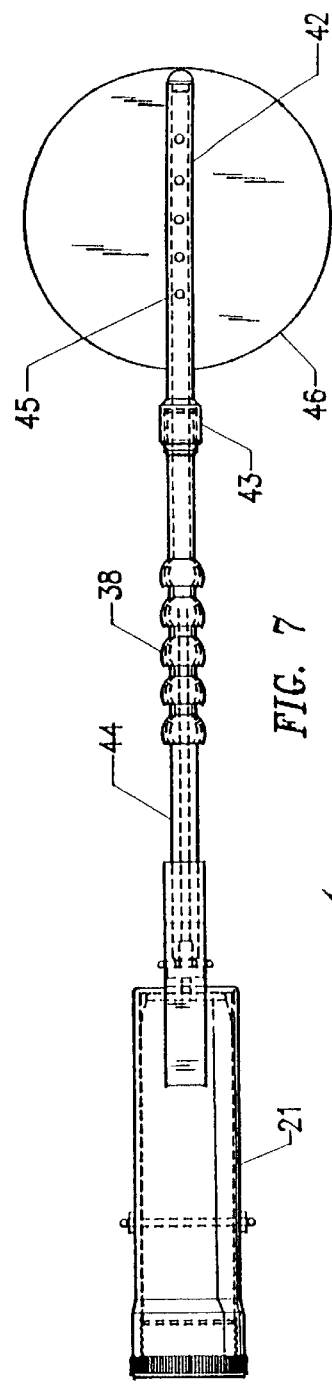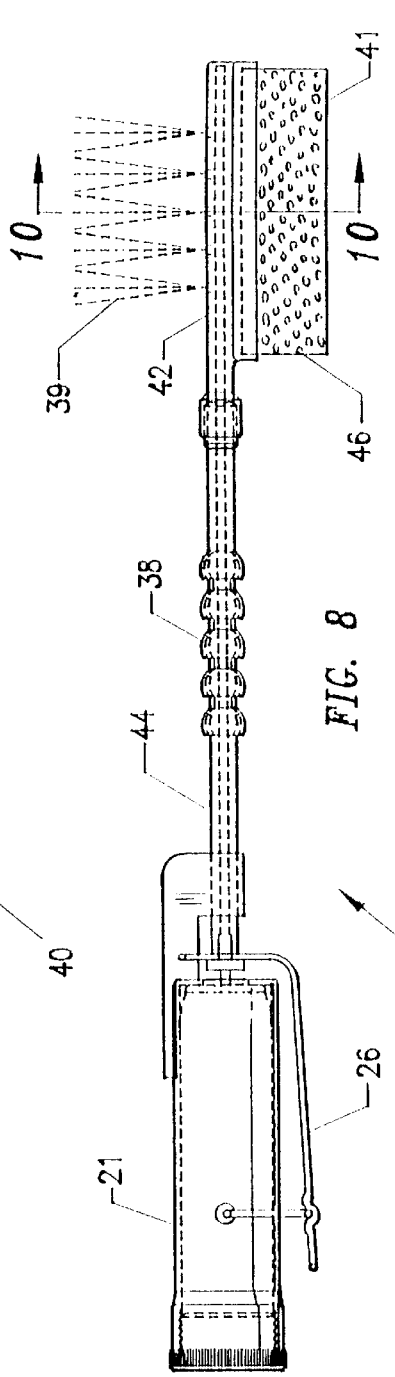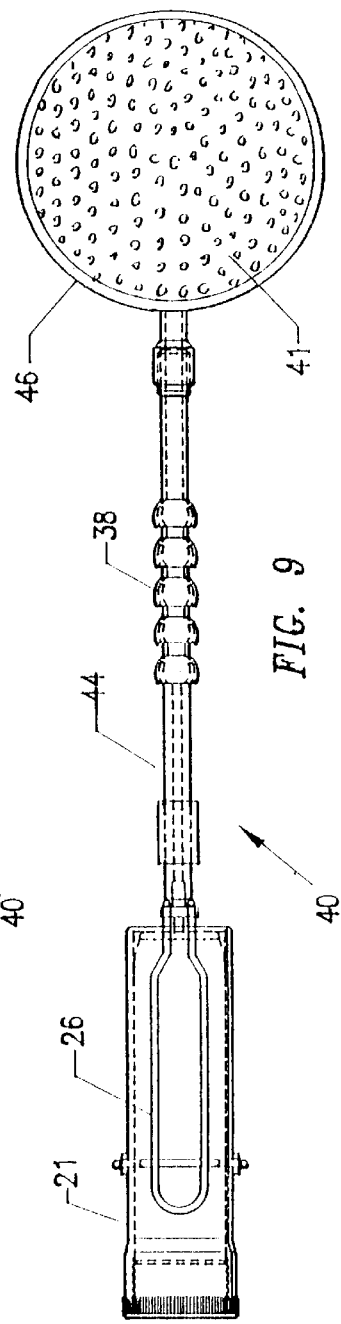

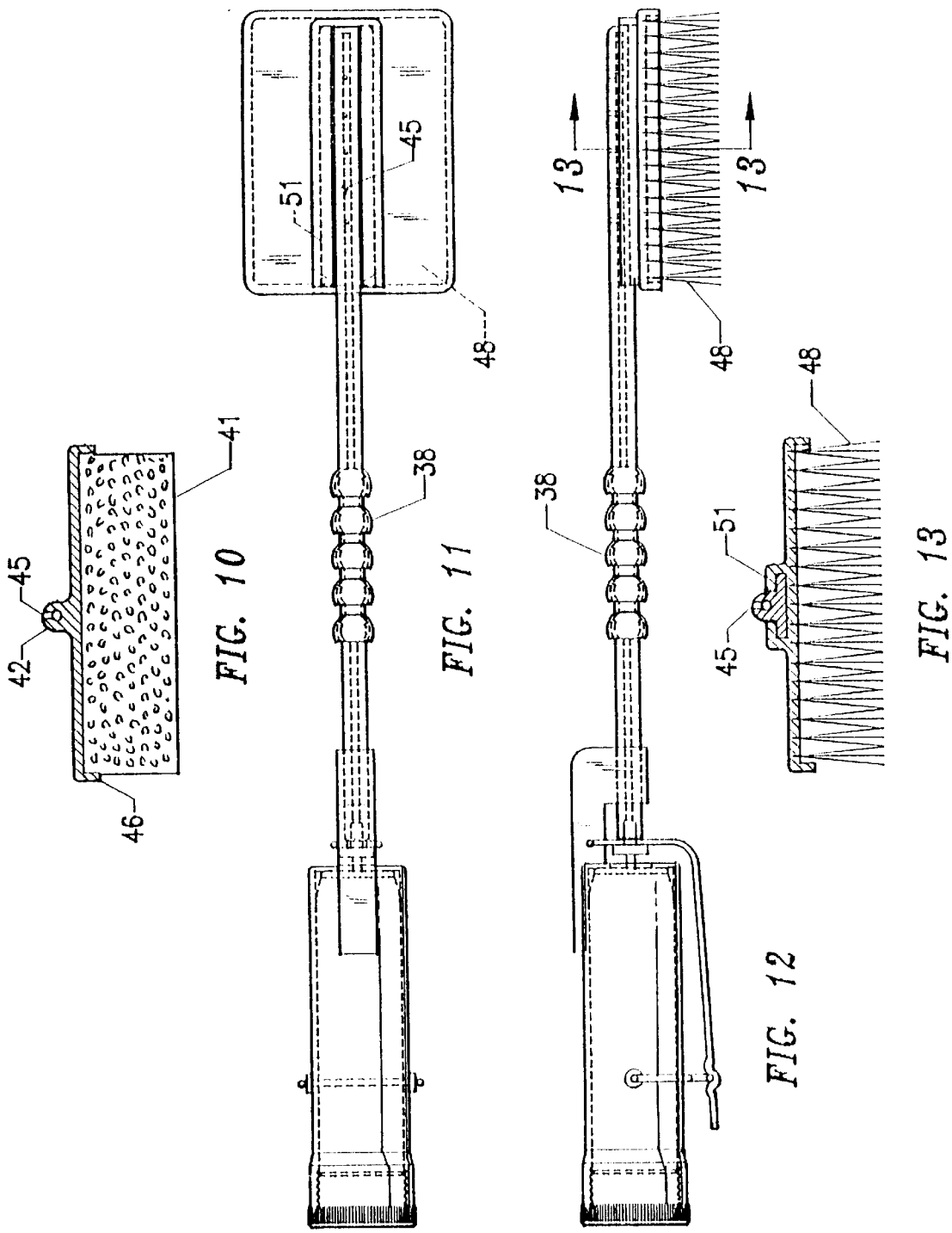

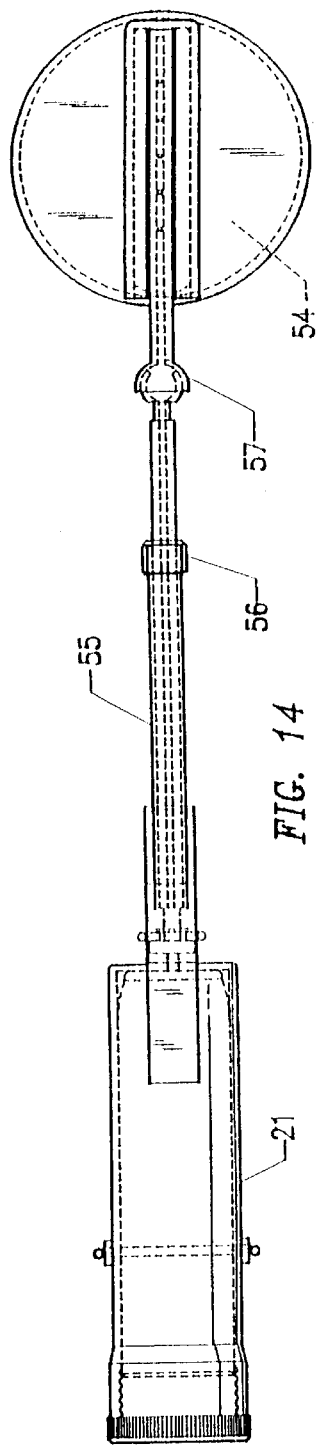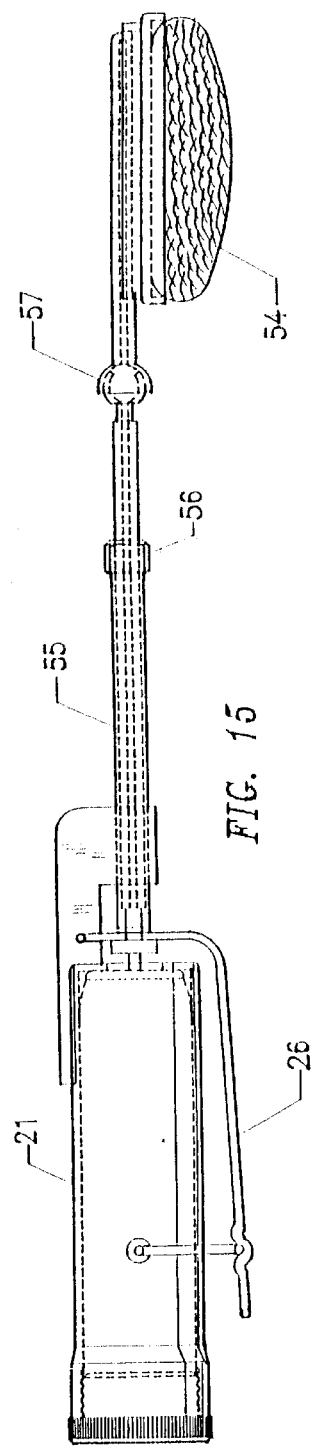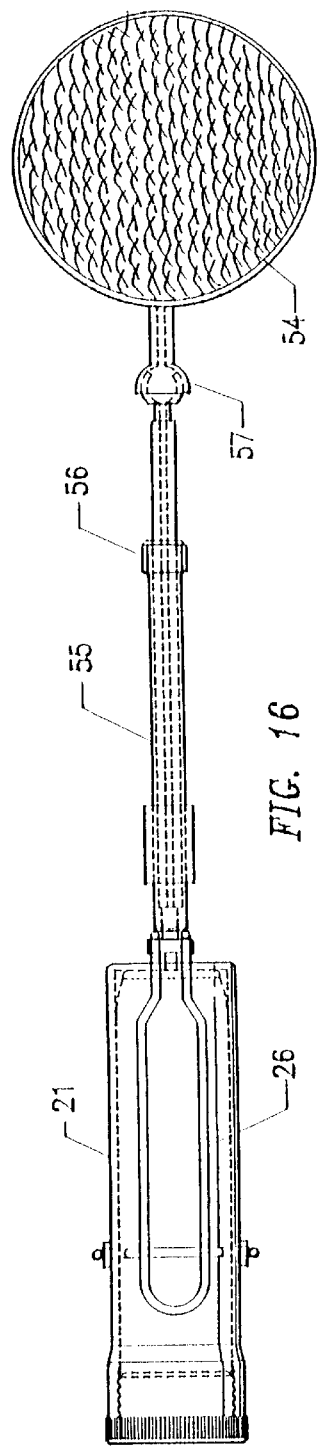

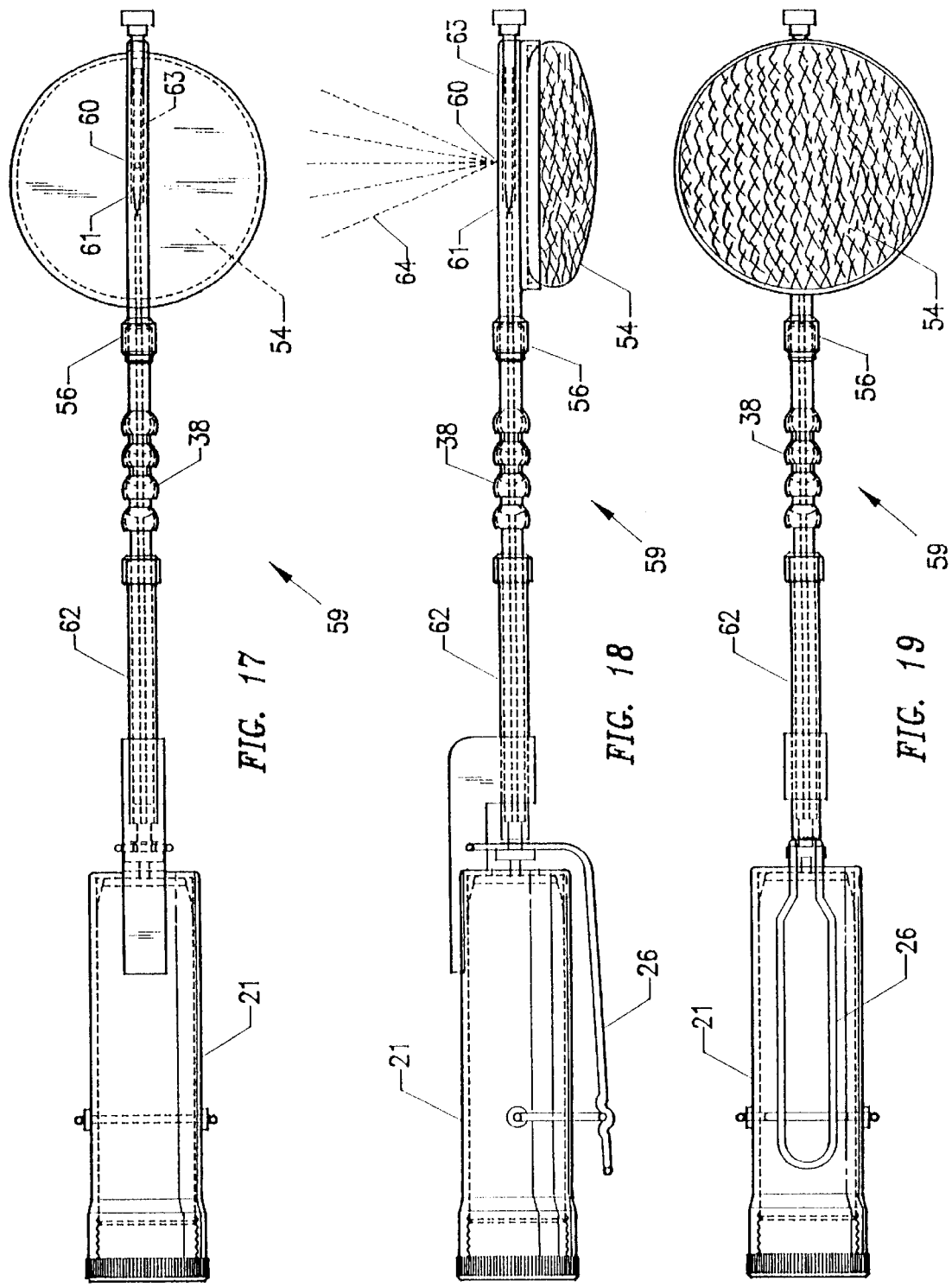

AEROSOL APPARATUS FOR HEALTH, HYGIENIC AND GROOMING NEEDS

RELATED APPLICATIONS

This application is a divisional of and claim the benefit of U.S. application Ser. No. 09/458,732, filed Dec. 13, 1999; and now U.S. Pat. No. 6,269,821.

FIELD OF THE INVENTION

This invention relates to a liquid dispensing and more particularly to an aerosol health and beauty products applicator apparatus for general use and benefit to physically disadvantaged persons.

BACKGROUND OF THE INVENTION

Many persons, including the elderly, arthritic, amputee, paralytic and bedridden persons are unable to care for their hygienic, health and grooming needs. They are unable to do so because many body areas are inaccessible or difficult to access for applying products such as sun screens, soaps, shampoos, deodorants, toilet waters, body lotions and medications.

The common methods of applying these products with hands or gauze fails these persons because of muscular and joint limitations. Another problem is that they are unable to open many of the containers of the health and beauty products. Consequently they rely on others, such as nurses, friends and family members for meeting their health, hygienic and grooming needs.

When help is unavailable, these needs are often unmet or met only after long delays. Since elderly and bedridden persons may generate strong body odors they need frequent scrubbing and grooming to avoid offending others.

In many cases, elderly and physically handicapped persons are confined in institutions, such as nursing homes, because they are unable to fill their health, hygienic and grooming needs. This reduces their quality of life and increases overall health costs.

Frequently, members of the general public need to relieve or apply lotions and medications to difficult to reach pruritic "itching" body areas. The upper and middle regions of the back are examples of such areas. Other areas present problems of access for applying sunscreens, or scrubbing for cleanliness before or after swimming or during bathing. An absence of sunscreen lotions or oils over the entire back region may result in severe sunburn.

SUMMARY OF THE INVENTION

The present invention overcomes all of the foregoing deficiencies by providing an improved, efficient, and easy to use apparatus and method for applying health, hygienic and beauty products.

The invention is suitable for use in private homes, nursing facilities, hospitals, while traveling, and at the beach. In addition to improving the health, hygiene and grooming of elderly and handicapped persons, overall health care costs can be lowered by reducing the services of health care professionals and employees, such as nurses and hospital attendants.

The invention generally comprises an aerosol container having an outlet end portion attached to one end portion of an extensible elongated tubular member, an applicator attached to an opposite end portion of the tubular member and a means within the tubular member for rotating about three mutually perpendicular axes. The applicator may be any of a variety of devices, such as an open cell sponge, brush, or loofah.

In a first aspect of the invention, an aerosol spray is dispersed through apertures in the tubular member into an open cell sponge. In a second aspect, an aerosol spray is discharged through apertures in the elongated tubular member on to a selected portion of a body.

The additional objects, features and benefits will be apparent by reference to the drawings and ensuing detailed description of a preferred embodiment which discloses the best mode contemplated in carrying out the invention. The exclusive rights which are claimed are set forth in the numbered claims following the detailed description of the preferred embodiment.

In employing the teaching of the present invention, a plurality of alternate constructions can be adopted to achieve the desired results and capabilities. In this disclosure, only several embodiments are discussed. However, these embodiments are intended as examples and should not be considered as limiting the scope of the invention.

BRIEF DESCRIPTION OF THE DRAWINGS

The invention will be better understood and further objects, characterizing features, details and advantages thereof will appear more clearly with reference to the diagrammatic drawings illustrating specific embodiments of the invention by way of non-limiting example only.

FIG. 1 is a plan view of an aerosol applicator apparatus according to the invention.

FIG. 2 is a right side view of the aerosol applicator apparatus.

FIG. 3 is a bottom view of the aerosol applicator apparatus.

FIG. 4 is an enlarged cross-sectional view taken on the line 4—4 in FIG. 1.

FIG. 5 is a cross-sectional view taken on the line 5—5 in FIG. 1.

FIG. 7 is a plan view of a second embodiment.

FIG. 8 is a right side view of the second embodiment.

FIG. 9 is a bottom view of the second embodiment.

FIG. 10 is an enlarged cross-sectional view taken on the line 10—10 in FIG. 8.

FIG. 11 is a plan view of a third embodiment.

FIG. 12 is a right side view of the third embodiment.

FIG. 13 is an enlarged cross-sectional view taken on the line 13—13 in FIG. 12.

FIG. 14 is a plan view of a fourth embodiment.

FIG. 15 is a right side view of the fourth embodiment.

FIG. 16 is a bottom view of the fourth embodiment.

FIG. 17 is a plan view of a fifth embodiment.

FIG. 18 is a right side view of the fifth embodiment.

FIG. 19 is a bottom view of the fifth embodiment.

DETAILED DESCRIPTION OF A PREFERRED EMBODIMENT

Figure 6:
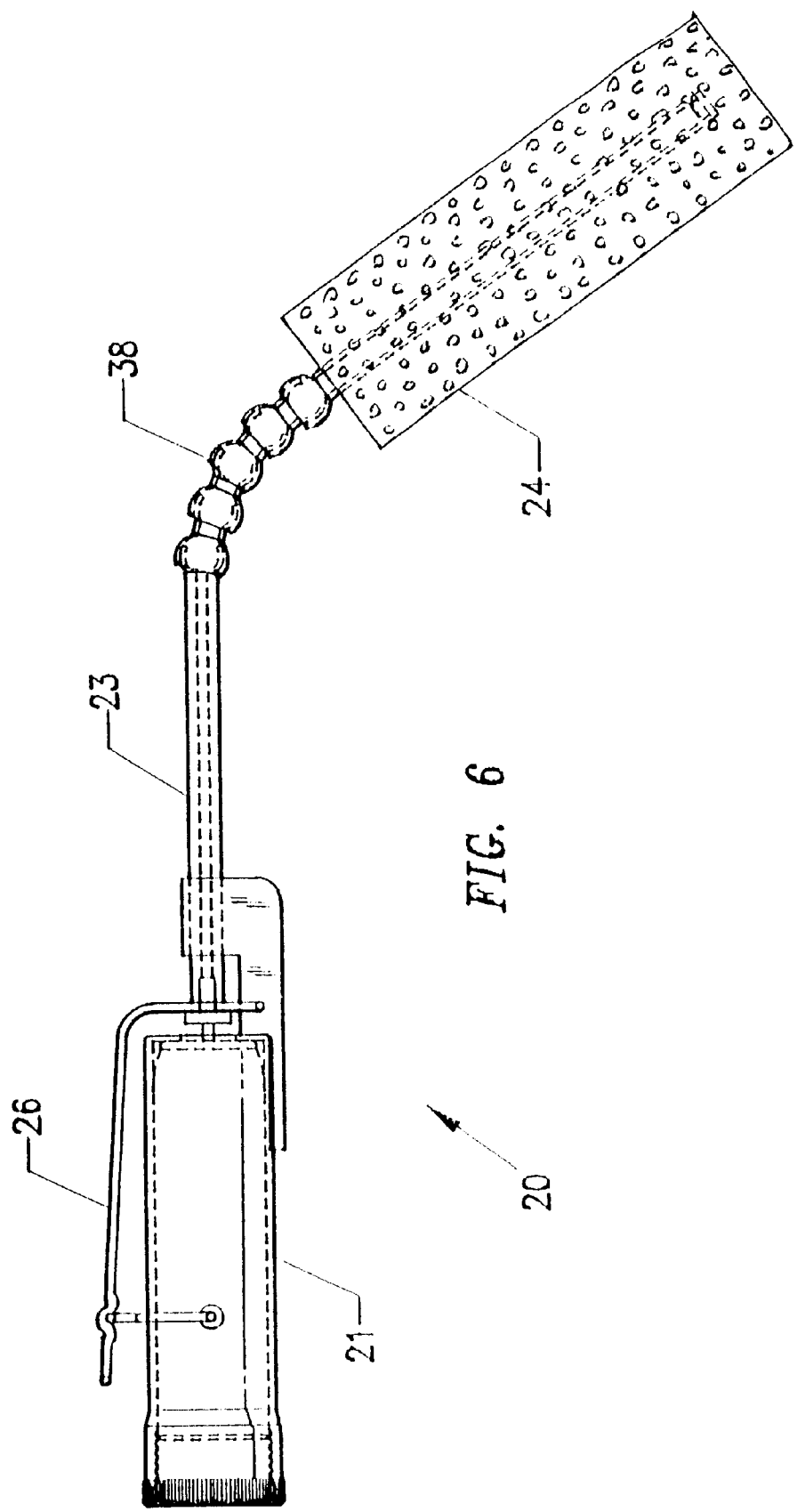
FIG. 6 is a right side view of an alternate configuration of the aerosol applicator apparatus.

Referring now to the drawings wherein like numerals designate like and corresponding parts throughout the several views, an aerosol applicator apparatus 20 is shown in FIGS. 1 through 6, inclusive, for applying liquid health, hygienic and grooming products. The apparatus 20 is comprised of a cylindrical housing 21, a replaceable aerosol cannister or cartridge 22, a slender tubular member 23, and an applicator 24.

At one end of the housing 21 is a removable closure 25 for installing and removing the aerosol cartridge 22. A wire handle 26 pivotally engages the housing 21 for opening an outlet valve 28 of the aerosol cartridge 22. The handle 26 pivots about point "A" of a bracket 29 which is attached to the housing 22 to open the valve. 28 Between the handle 26 and the housing 21 is a wire blocking member 30 for preventing a movement of the handle 26 when the apparatus 20 is not in use. The wire blocking member 30 is selectively pivotal about point "B" from an unblocking position 31 adjacent to the housing 21 to a blocking position 32 away from the housing 21.

An inlet portion 33 of the elongated tubular member 23 is attached to the bracket 29 and engages an outlet portion 34 of the aerosol cartridge 22. When the handle 26 is squeezed in the direction of arrow "C" to open the aerosol valve 28, an aerosol spray 35 containing a health, hygienic or grooming product is discharged into the elongated tubular member 23.

An outlet portion 36 of the tubular member 23 is surrounded by an elliptical resilient open cell pad 37. An aerosol spray (not shown) is dispersed through apertures 47 in the outlet portion 36 of the tubular member 23 into the open cell pad 37. The pad 37 is used for applying the aerosol spray and scrubbing a body area.

One important feature of the apparatus is a group of ball and socket joints 38 in the tubular member 23. They allow the applicator 24, as shown in FIG. 6, to be rotated about three mutually perpendicular axes to reach a variety of body areas. The ball and socket joints 38 are made of resilient plastic materials, whereby their members can be forcibly engaged to prevent leakage and to provide sufficient joint friction for maintaining the orientation of the applicator 24.

The preferred method of using the applicator apparatus of FIGS. 1 through 6 is as follows. The replaceable aerosol cartridge 22 is inserted into the housing 21 by removing the closure 25 at the end of the housing 21. The applicator 24 is properly positioned by rotating and flexing the ball and socket joints 38 to suit a specific body area. After the user is satisfied with the orientation of the applicator 24, the handle 26 is squeezed to disperse a portion of the aerosol suspension into the open cell pad 37. The absorbed aerosol product is then applied to the selected body area with the cellular pad 37 and the pad 37 is used to scrub or cleanse the selected area.

An alternate embodiment 40 of the invention is shown in FIGS. 7 through 10, inclusive. In this embodiment 40, a detachable circular resilient cellular pad 41 is mounted to an outlet end portion of an elongated tubular member 44 with a coupling 43. The coupling 43 allows a variety of applicators to be attached to the tubular member 44.

In the outlet end portion 42 of the tubular member 44 is a linear arrangement of apertures 45 through which an aerosol spray 39 is discharged when the handle 26 is squeezed. The cellular pad 41 is used to spread and scrub the affected area after the aerosol spray is applied.

The preferred method of using the second embodiment 40 differs from the method of the first embodiment 20 as follows. The applicator apparatus 40 may be used in two ways. The first way is to apply a health or beauty product, such as a soap or sunscreen, directly to the cellular pad 41, to orient the applicator 46 and then apply the product with the pad 41 to a selected body area. The aerosol cartridge 22 is used to apply a different type of product, such as a body lotion to the selected area.

The second way is to apply a health or beauty product with the aerosol cartridge 22 to a body area. The applicator 46 is then oriented to align the pad 41 with the body area and the aerosol product is spread over the body area with the pad 41. If required, the body area is cleansed or scrubbed with the pad 41.

In FIGS. 11 through 13, the cellular pad 41 of FIGS. 7 through 9 is replaced with a rectangular brush 48. The rectangular brush 48 is attached to an outlet end portion of an elongated tubular member 55 with a tongue and groove attachment 51. In FIGS. 14 through 16, a circular loofah 54 is mounted on the elongated tubular member 50 with a threaded coupling 56. A single ball and socket joint 57 allows the loofah 54 to be rotated about three mutually perpendicular axes. The elongated tubular member 55 is an extensible member to increase the utility of the invention.

In FIGS. 17 through 19, an embodiment 59 is shown wherein an aerosol spray is discharged through a single aperture 60 in an outlet end portion 61 of an elongated tubular member 62. A needle valve 63 is provided in the distal end 61 of the tubular member 62 to regulate the amount of aerosol spray 64 which is discharged through the aperture 60.

From the foregoing it will be appreciated that our invention provides a novel apparatus and method which allows physically disadvantaged as well as persons who are not physically disadvantaged to efficiently apply liquid and beauty products to selected areas of their bodies. It will also be appreciated that our invention is particularly useful to elderly and physically disadvantaged persons who heretofore have required the assistance of others. It will be still further appreciated that our invention can be used at a variety of places, such as beaches, showers, bathtubs, hospitals and nursing homes.

Although only several embodiments have been illustrated and described for purposes of disclosure and enabling persons to practice the invention, it is not our intention to limit our invention to these embodiments, since other embodiments can be derived by obvious substitutions, changes in shape, elimination and additions of parts, and changes in the arrangement of parts without departing from the spirit thereof.

We claim:

1. An aerosol apparatus for storing and applying a health or beauty product to a selected area of a person's body, comprising: a replaceable cartridge for storing and dispersing an aerosol suspension of a health or beauty product, said cartridge having an outlet end portion and a valve for sealing said aerosol suspension in said cartridge; a slender, substantially elongated external tubular member for applying said health or beauty product to a remote or difficult to access body areas, said substantially elongated tubular member having an inlet end portion operatively connected to said outlet end portion of said cartridge and an opposite end portion for connecting an applicator; a detachable applicator for receiving a portion of said suspension from said cartridge and applying said health or beauty product to said selected portion of said person's body; and a means for opening said valve; and a means for rotating said applicator relative to said cartridge about at least one axis.

2. The apparatus recited in claim 1 wherein said applicator is an open cell pad.

3. The apparatus recited in claim 2 wherein an end portion of said elongated tubular member has a plurality of small apertures for dispersing said aerosol product into said open cell pad.

4. The apparatus recited in claim 1 wherein said applicator is a brush.

5. The apparatus recited in claim 1 wherein said applicator is a loofah.

6. The apparatus recited in claim 1 wherein said rotating means comprises at least one ball and socket joint in said tubular member for rotating said applicator about three mutually perpendicular axes.

7. The apparatus recited in claim 1 wherein said rotating means comprises a plurality of ball and socket joints in said elongated tubular member for rotating said applicator about three mutually perpendicular axes.

8. The apparatus as recited in claim 1 wherein an end portion of said tubular member has at least one aperture for discharging a spray of said aerosol suspension.

9. The apparatus recited in claim 1 wherein said applicator is elliptical.

10. The apparatus as recited in claim 1 wherein said applicator is rectangular.

11. The apparatus as recited in claim 1 wherein said applicator is circular.

12. The apparatus recited in claim 1 wherein an outlet end portion of said elongated tubular member has at least one aperture for discharging a spray of said aerosol suspension on said selected body area.

13. The apparatus recited in claim 1 wherein said slender tubular member is extensible.

14. An aerosol apparatus for storing and applying a health or beauty product to a selected area of a person's body, comprising: a housing for storing a replaceable aerosol cartridge; a replaceable aerosol cartridge in an interior portion of said housing, said cartridge having an aerosol suspension of a health or beauty product, an outlet portion and a normally closed valve for discharging an aerosol spray of said health or beauty product from said outlet portion of said cartridge; a handle pivotally attached to said housing for opening said normally closed valve; a means for selectively preventing a movement of said handle; a slender, external, substantially elongated tubular member for applying said health or beauty product to a remote or difficult to access body areas, said substantially elongated tubular member having an inlet end portion operatively connected to said outlet end portion of said cartridge, at least one aperture in said slender tubular member for discharging a portion of said aerosol suspension and a detachable applicator for spreading said aerosol product over said selected body portion.

15. An aerosol apparatus for storing and applying a health or beauty product to a selected remote or difficult to access area of a person's body, comprising: a cartridge for storing and dispersing an aerosol suspension of a health or beauty product, said cartridge having an outlet end portion and a valve for sealing said aerosol suspension in said cartridge; a slender, substantially elongated tubular member for applying said health or beauty product to a remote or difficult to access body area, said substantially elongated tubular member having an inlet end portion operatively connected to said outlet end portion of said cartridge and an opposite end portion for connecting an applicator; a detachable applicator for receiving a portion of said aerosol suspension from said cartridge and applying said health or beauty product to said selected portion of said person's body; at least one ball and socket joint in said tubular member for rotating said applicator about three mutually perpendicular axes; and a means for opening said valve.

16. An aerosol apparatus for storing and applying a health or beauty product to a selected remote or difficult to access area of a person's body, comprising: a cartridge for storing and dispersing an aerosol suspension of a health or beauty product, said cartridge having an outlet end portion and a valve for sealing said aerosol suspension in said cannister cartridge; a slender, substantially elongated tubular member for applying said health or beauty product to a remote or difficult to access body area, said substantially elongated tubular member having an inlet end portion operatively connected to said outlet end portion of said cartridge and an opposite end portion for connecting an applicator; a detachable applicator for receiving a portion of said aerosol suspension from said cartridge and applying said health or beauty product to said selected portion of said person's body; a means for rotating said applicator relative to said cartridge about at least one axis; and a means for opening said valve.

* * * * *